United States Patent [19]

Kvita et al.

[11] 4,132,716
[45] Jan. 2, 1979

[54] IMIDYL-BENZENE-DICARBOXYLIC AND -TRICARBOXYLIC ACID DERIVATIVES

[75] Inventors: Vratislav Kvita, Muttenz; Roland Darms, Therwil; Gerd Greber, Binningen, all of Switzerland

[73] Assignee: Ciba-Geigy Corporation, Ardsley, N.Y.

[21] Appl. No.: 696,348

[22] Filed: Jun. 15, 1976

[30] Foreign Application Priority Data

Jun. 18, 1975 [CH] Switzerland ............ 7953/75

[51] Int. Cl.² .................. C07D 405/02; C07D 207/44
[52] U.S. Cl. .................. 260/326.34; 260/326 A; 260/326 C; 260/326.26; 260/326.27; 260/326.29; 260/326.32; 260/326.41; 260/326.5 FM; 526/236; 260/823
[58] Field of Search ............ 260/326.41, 326.34, 260/326.43, 326.5 FM, 326.26, 78 UA, 47 UA; 526/263

[56] References Cited

U.S. PATENT DOCUMENTS

| 2,726,981 | 12/1955 | Wolf et al. | 260/326.5 FM |
|---|---|---|---|
| 2,962,504 | 11/1960 | Walker et al. | 260/326.5 FM |
| 3,039,860 | 6/1962 | Andress et al. | 260/326.41 |
| 3,397,210 | 8/1968 | Michalowicz | 260/376.5 FM |
| 3,465,001 | 9/1969 | Bolhofer et al. | 260/326.41 |
| 3,465,002 | 9/1969 | Bolhofer et al. | 260/326.41 |
| 3,538,114 | 11/1970 | Himmele et al. | 260/326.5 FM |
| 3,557,132 | 1/1971 | Hermann et al. | 260/326.5 FM |
| 3,660,408 | 5/1972 | Ackerman | 260/326.5 FM |
| 3,816,451 | 6/1974 | Crovetti et al. | 260/326.5 FM |
| 3,878,224 | 4/1975 | Matsui et al. | 260/326 R |
| 3,948,941 | 4/1976 | Patton | 260/326.5 FM |
| 3,984,435 | 10/1976 | Matsui et al. | 260/326 A |
| 4,043,986 | 8/1977 | Gruffaz et al. | 260/47 UA |

Primary Examiner—Nicholas S. Rizzo
Assistant Examiner—Mary C. Lee
Attorney, Agent, or Firm—Luther A. R. Hall

[57] ABSTRACT

New imidyl-benzene-dicarboxylic and -tricarboxylic acid derivatives, in particular 5-maleimidyl-trimellitic acid derivatives and 3,5-bis-(maleimidyl)-phthalic acid derivatives, and a process for their manufacture are described. These imidyl-benzene-dicarboxylic and -tricarboxylic acid derivatives are suitable for the manufacture of crosslinkable polymers, above all polycondensation and polymerization products, which are distinguished by good processability and good solubility in customary organic solvents. Imidyl compounds, according to the definition, which have anhydride groups can also be used as curing agents for optionally modified epoxide resins.

7 Claims, No Drawings

IMIDYL-BENZENE-DICARBOXYLIC AND -TRICARBOXYLIC ACID DERIVATIVES

The present invention relates to new imidyl-benzene-dicarboxylic and -tricarboxylic acid derivatives and a process for their manufacture.

The new imidyl-benzene-dicarboxylic and -tricarboxylic acid derivatives correspond to the formula I

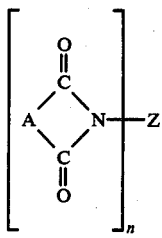 (I)

wherein A denotes a radical of the formula

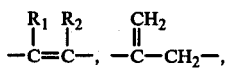

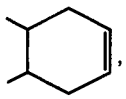,

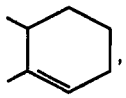,

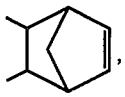, or

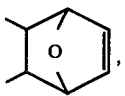, $R_1$ and $R_2$ independently of one another denote hydrogen, chlorine or bromine, n denotes the number 1 or 2 and, when n = 1, Z denotes a radical of the formula

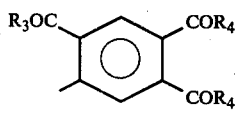

and, when n = 2, Z denotes a radical of the formula

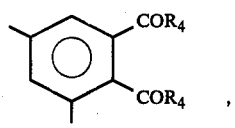

$R_4$ denotes a hydroxyl group, an unsubstituted or substituted phenoxy group, an alkoxy group with 1-18 carbon atoms or a $-O^-M^+$ group, or the two $R_4$s conjointly denote the —O— grouping and, when $R_4$ represents an unsubstituted or substituted phenoxy group or an alkoxy group with 1-18 carbon atoms, or the two $R_4$s conjointly represent —O—, $R_3$ denotes a chlorine atom, a hydroxyl group, an unsubstituted or substituted phenoxy group, an alkoxy group with 1-18 carbon atoms or a $-O^-M^+$ group and, when $R_4$ represents a hydroxyl group, $R_3$ denotes a hydroxyl group, an unsubstituted or substituted phenoxy group or an alkoxy group with 1-18 carbon atoms and, when $R_4$ represents a $-O^-M^+$ group, $R_3$ denotes a $-O^-M^+$ group, an unsubstituted or substituted phenoxy group or an alkoxy group with 1-18 carbon atoms and $M^+$ denotes an alkali metal cation, a trialkylammonium cation with 3-24, and especially 3-12, carbon atoms or a quaternary ammonium cation.

The new imidyl-benzene-dicarboxylic and -tricarboxylic acid derivatives can be manufactured, according to the invention, by reacting an amine of the formula II

 (II)

in at least the stoichiometric amount with an anhydride of the formula III

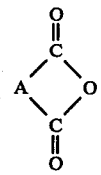 (III)

to give a compound of the formula IV

 (IV)

wherein A and n have the meaning indicated under formula I and, when n = 1, Z' denotes a radical of the formula

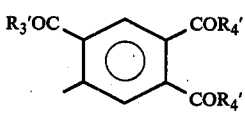

and, when n = 2, Z' denotes a radical of the formula

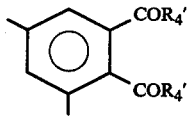

wherein $R_4'$ denotes a hydroxyl group, an unsubstituted phenoxy group or a substituted phenoxy group which is free from electronegative substituents, an alkoxy group with 1-18 carbon atoms or a $-O^-M^+$ group, and, when $R_4'$ represents a phenoxy or alkoxy group according to the definition, $R_3'$ denotes a hydroxyl group, an unsubstituted phenoxy group or a substituted phenoxy group which is free from electronegative substituents, an alkoxy group with 1-18 carbon atoms or a $-O^-M^+$ group and, when $R_4'$ represents a hydroxyl group, $R_3'$ denotes a hydroxyl group or a phenoxy or alkoxy group according to the definition and, when $R_4'$ represents a $-O^-M^+$ group, $R_3'$ denotes a $-O^-M^+$ group or a phenoxy or alkoxy group according to the definition and $M^+$ has the meaning indicated under formula I, subsequently cyclising the compound of the formula IV and optionally converting the resulting compound of the formula I into another derivative, according to the definition, of the formula I.

Preferably, A represents a radical of the formula

and especially a radical of the formula —CH=CH—. If $R_3$, $R_3'$, $R_4$ or $R_4'$ represent substituted phenoxy groups, the latter are, in particular, phenoxy groups which are substituted by nitro groups or alkyl or alkoxy groups with 1 or 2 carbon atoms or by halogen atoms, above all chlorine or fluorine, such as the 2-, 3- or 4-nitrophenoxy group, the 2,4- or 3,5-dinitrophenoxy group, the 3,5-dichlorophenoxy group, the pentachlorophenoxy group or the 2-methyl- or 2-methoxy-phenoxy group.

According to the definition, substituted phenoxy groups $R_3'$ and $R_4'$ are free from electronegative substituents, such as nitro groups or halogen atoms. End products of the formula I, wherein $R_3$ and/or $R_4$ denote phenoxy groups which contain electronegative substituents of this type, are appropriately manufactured — as indicated further below — from the corresponding anhydrides, acid anhydrides or acid chloride-anhydrides or by trans-esterification.

Alkoxy groups $R_3$, $R_3'$, $R_4$ or $R_4'$ can be straight-chain or branched. Examples which may be mentioned are: the methoxy, ethoxy, n-propoxy, isopropoxy, n-butoxy, tert.-butoxy, hexyloxy, octoxy, decyloxy, dodecyloxy, tetradecyloxy and octadecyloxy group.

If $R_3$, $R_3'$, $R_4$ or $R_4'$ denote a $—O^-M^+$ group, $M^+$ represents, for example, the lithium, sodium, potassium, trimethylammonium, triethylammonium, methyl-diethylammonium, tri-n-octylammonium, benzyltrimethylammonium or tetramethylammonium cation. $M^+$ preferably represents the sodium cation.

Compounds of the formula I wherein A represents the radical

and above all the radical —CH=CH— and, when n = 1, Z represents a radical of the formula

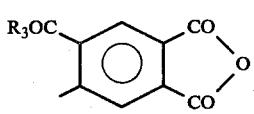

and, when n = 2, Z represents a radical of the formula

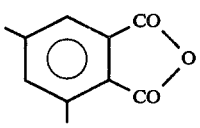

and $R_3$ denotes a chlorine atom or an alkoxy group with 1–12 carbon atoms and especially 1–4 carbon atoms are particularly preferred.

The starting materials of the formulae II and III are known or can be manufactured in a manner which is in itself known.

Appropriately, the free acids, esters according to the definition or salts, especially the Na salts, are used as the amines and diamines of the formula II. The use of amines or diamines of the formula II wherein $R_3'$ denotes —OH or an alkoxy group with 1–12, and especially 1–4, carbon atoms and the $R_4$'s denote —OH groups is preferred.

The aminobenzene-dicarboxylic and -tricarboxylic acids of the formula II, and their derivatives, can be employed as such or can be manufactured in situ by reducing the corresponding nitrobenzene-dicarboxylic or -tricarboxylic acids, or derivatives thereof, and used further without intermediate isolation.

Examples which may be mentioned of suitable anhydrides of the formula III are: maleic anhydride, itaconic anhydride, chloromaleic anhydride, 2,3-dichloromaleic anhydride, 2,3-dibromomaleic anhydride, 4- and 2-cyclohexene-1,2-dicarboxylic acid anhydride, 3,6-endomethylene-1,2,3,6-tetrahydrophthalic anhydride (nadic anhydride) and 3,6-endoxo-1,2,3,6-tetrahydrophthalic anhydride. Nadic anhydride and, above all, maleic anhydride are preferably used.

The reaction of the amines of the formula II with the anhydrides of the formula III can be carried out in the melt, by heating the reactants to temperatures of up to about 150° C., or in an aqueous, aqueous-organic or organic medium, in which case the reaction is appropriately carried out at temperatures between about 0° C. and 50° C., especially between about 15° C. and 25° C.

Appropriately, the anhydride of the formula III is employed in the stoichiometric amount or in a slight excess over the amine of the formula II, for example in an up to about 20% molar excess. The reaction is advantageously carried out in an organic medium. Organic solvents which can be used are, above all, aprotic organic solvents. Examples of suitable aprotic organic solvents are: optionally chlorinated aliphatic or aromatic hydrocarbons, such as benzene, toluene, methylene chloride, chloroform, carbon tetrachloride, 1,1,2-trichloroethane, 1,2-dichloroethylene and chlorobenzene; aliphatic and cycloaliphatic ketones, such as acetone, methyl ethyl ketone, cyclopentanone and cyclohexanone; cyclic ethers, such as tetrahydrofurane, tetrahydropyrane and dioxane; cyclic amides, such as N-methyl-2-pyrrolidone, N-acetyl-2-pyrrolidone and N-methyl-ε-caprolactam; N,N-dialkylamides of aliphatic monocarboxylic acids with 1–3 carbon atoms in the acid part, such as N,N-dimethylformamide, N,N-dimethylacetamide, N,N-diethylacetamide and N,N-dimethylmethoxyacetamide; alkyl esters of aliphatic monocarboxylic acids with a total of 2–6 carbon atoms, such as formic acid methyl, ethyl or n-butyl ester or acetic acid methyl, ethyl or n-butyl ester; hexamethylphosphoric acid triamide (hexametapol); N,N,N',N'-tetramethylurea; tetrahydrothiophene dioxide (sulpholane); and dialkylsulphoxides, such as dimethylsulphoxide and diethylsulphoxide. Mixtures of solvents of this type can also be employed. Dioxane is the preferred solvent.

When the reaction has ended, the amide-acid derivatives of the formula IV are isolated in a customary manner, by filtration or by stripping off the solvent, and optionally purified, for example by washing with water and/or suitable solvents, such as methanol, dioxane, diethyl ether, methylene chloride and chloroform, or by recrystallisation or extraction with suitable organic solvents, such as ethyl acetate. Solvent mixtures can also be used.

However, the amide-acids of the formula IV can also be cyclised direct, without intermediate isolation, to give the imidyl compounds of the formula I. The cyclisation of the amide-acids of the formula IV to compounds of the formula I can be carried out, in a manner which is in itself known, chemically, that is to say using catalysts which are in themselves known for forming imides and, optionally anhydrides, and/or using dehydrating agents, and/or by the action of heat.

The cyclisation is generally carried out at temperatures between about 40 and 120° C., preferably at 70°–90° C., with the addition of suitable catalysts and/or dehydrating agents and optionally in the presence of an aprotic organic solvent.

Dehydrating agents which can be used are, above all, anhydrides of aliphatic monocarboxylic acids which have 2–5 carbon atoms and are optionally substituted by halogen atoms or alkyl groups, such as acetic anhydride, propionic anhydride, butyric anhydride and valeric anhydride and trichloro-, trifluoro-, trimethyl-, triethyl- and tri-n-butyl-acetic anhydride. Acetic anhydride is the preferred dehydrating agent.

Catalysts which can be used are, for example, alkaline earth metal salts or alkali metal salts of aromatic monocarboxylic acids or of aliphatic monocarboxylic acids with 1–3 carbon atoms, such as sodium benzoate, sodium salicylate, calcium formate and sodium formate, calcium acetate, magnesium acetate, sodium acetate and potassium acetate and sodium propionate; bases, such as trimethylamine and triethylamine, or nickel salts or nickel complexes, such as nickel 2-acetate or nickel acetylacetonate.

Preferred catalysts are sodium acetate, nickel 2-acetate and triethylamine.

Depending on the nature of the amide-acid of the formula IV which is to be cyclised, it can be advantageous additionally to use an aprotic organic solvent, above all benzene or toluene. The cyclisation to compounds of the formula I can also be carried out by the action of heat, by heating to temperatures of about 40° C. to 150° C. The compounds of the formula I obtained after the cyclisation can, if desired — and depending on the nature of the amines of the formula II which have been used — be converted into other derivatives, according to the definition, of the formula I in a manner which is in itself known, for example as follows:

free acids ($R_4$ = —OH) by hydrolysis of compounds of the formula I wherein the two $R_4$s conjointly form an —O— grouping, acid chlorides ($R_3$ = —Cl) by reaction of compounds of the formula I wherein $R_3$ = —OH or —O$^-$M$^+$ with suitable chlorinating agents, such as thionyl chloride, oxalyl chloride and phosgene, esters ($R_3$ or $R_4$ = unsubstituted or substituted phenoxy or alkoxy) by reaction of compounds of the formula I wherein $R_3$ = —Cl or —OH, or the two $R_4$s conjointly = —O—, with corresponding alcohols or by trans-esterification of compounds of the formula I wherein $R_3$ or $R_4$ = unsubstituted or substituted phenoxy or alkoxy, and salts ($R_3$ or $R_4$ = —O$^-$M$^+$) by reaction of the free acids with corresponding bases, such as NaOH.

Furthermore, it is possible to convert compounds of the formula I wherein A represents —CH=CH— into compounds of the formula I wherein A represents the group

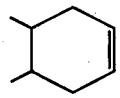

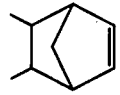

or

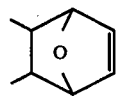

by an addition reaction with 1,3-butadiene, cyclopentadiene or furane. The addition reaction is appropriately carried out in an inert organic solvent of the abovementioned type, for example in benzene or toluene.

The imidylbenzene-dicarboxylic and -tricarboxylic acid derivatives of the formula I are obtained in the form of colourless to slightly yellowish crystals and can be isolated, and purified, in the customary manner, for example by extraction and/or recrystallisation from suitable organic solvents, such as benzene, methanol, glacial acetic acid, ethyl acetate, cyclohexane, dioxane, diethyl ether or methylene chloride or mixtures of such solvents.

Compounds of the formula I wherein Z denotes a radical of the formula

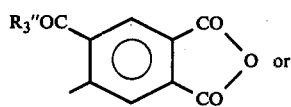 or

and $R_3''$ denotes a hydroxyl group, an unsubstituted or substituted phenoxy group or an alkoxy group with 1–18 carbon atoms, and especially 1–12 carbon atoms, are valuable curing agents for optionally modified epoxide resins. The products or materials cured with these compounds are distinguished by good mechanical, thermal and/or electrical properties, such as a high heat distortion point and/or a low dielectric loss factor.

The invention thus also relates to curable mixtures which are suitable for the production of mouldings, impregnated products, coatings, adhesive bonds and the like. These mixtures are characterised in that they contain (a) a polyepoxide compound and (b) as the curing agent, at least one compound of the formula I, wherein Z has the abovementioned meaning and what has been stated under formula I applies in respect of A and n, and (c) optionally at least one vinyl compound.

Curable mixtures which contain, as the curing agent (b), at least one compound of the formula I wherein A denotes the radical

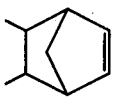

or, in particular, the radical —CH═CH—, n denotes the number 1 and Z denotes a radical of the formula

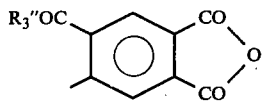

in which $R_3''$ represents an alkoxy group with 1-12, especially 1-4, carbon atoms are preferred.

When vinyl compounds (c) are also used it is particularly advantageous when these vinyl compounds are linked covalently to the epoxide resin by copolymerisation with the unsaturated curing agents (b).

Appropriately, 0.5-1.5 mols, preferably about 0.9-1.0 mol, of a curing agent (b) or of a mixture of a curing agent (b) and a vinyl compound (c) are used per 1 equivalent of epoxide group in the polyepoxide compound (a).

Vinyl compounds (c) which can be used are, for example, those of the formula V

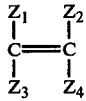 (V)

wherein $Z_1$ and $Z_3$ each represent hydrogen, $Z_2$ represents hydrogen, chlorine or methyl and $Z_4$ represents hydrogen, methyl, ethyl, chlorine, —CN, —COOH, —CONH$_2$, phenyl, methylphenyl, methoxyphenyl, cyclohexyl, pyridyl, imidazolyl, pyrrolidonyl, -COO-alkyl with 1-12 carbon atoms in the alkyl part, -COO-phenyl,

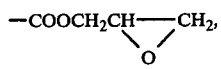

—COO-alkyl-OH with 1-3 carbon atoms in the alkyl part, —OCO-alkyl with 1-4 carbon atoms in the alkyl part, OCO-phenyl, -CO-alkyl with 1-3 carbon atoms in the alkyl part, alkoxy with 1-6 carbon atoms, phenoxy, —CH═CH$_2$ or

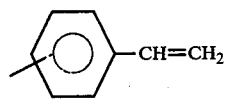

or $Z_1$ and $Z_2$ each represent hydrogen and $Z_3$ and $Z_4$ conjointly form the grouping

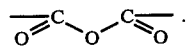

Examples which may be mentioned of vinyl compounds of this type are: ethylene, propylene, 1-butene, isoprene, 1,4-butadiene, vinyl chloride, vinylidene chloride, acrylic acid, methacrylic acid, acrylonitrile, methacrylonitrile, chloroacrylonitrile, styrene, methylstyrenes which are substituted in the nucleus, 4-methoxystyrene, vinylcyclohexane, acrylic acid methyl, ethyl, isopropyl, 2-ethylhexyl and phenyl ester and methacrylic acid methyl, ethyl, isopropyl, 2-ethylhexyl and phenyl ester, acetic acid vinyl ester and propionic acid vinyl ester, acrylic acid 2,3-epoxypropyl ester and methacrylic acid 2,3-epoxypropyl ester, benzoic acid vinyl ester, 2-vinylpyridine, 4-vinylpyridine, vinylimidazole, vinylpyrrolidone, methyl vinyl ketone, ethyl vinyl ketone, ethyl vinyl ether, n-butyl vinyl ether and divinylbenzene.

Mixtures of several vinyl compounds of the formula V can also be used.

Vinyl compounds of the formula V wherein $Z_1$ and $Z_3$ each denote hydrogen, $Z_2$ denotes hydrogen or methyl and $Z_4$ denotes -COO-alkyl with 1-10 carbon atoms in the alkyl part, or $Z_1$, $Z_2$ and $Z_3$ each denote hydrogen and $Z_4$ denotes —CN, chlorine, phenyl or —OCOCH$_3$, are preferably used.

Polyepoxide compounds (a) which can be used are all those which can be cured with anhydride curing agents. The following may be mentioned in particular: alicyclic polyepoxides, such as epoxyethyl-3,4-epoxycyclohexane (vinylcyclohexenediepoxide), limonene diepoxide, dicyclopentadiene diepoxide, bis-(3,4-epoxycyclohexylmethyl) adipate, 3',4'-epoxycyclohexylmethyl 3,4-epoxycyclohexanecarboxylate, 3',4'-epoxy-6'-methylcyclohexylmethyl 3,4-epoxy-6-methylcyclohexanecarboxylate, 3-(3',4'-epoxycyclohexyl)-2,4-dioxaspiro-(5,5)-8,9-epoxyundecane and 3-(glycidyloxy-ethoxyethyl)-2,4-dioxaspiro(5,5)-8,9-epoxyundecane; di- or poly-glycidyl ethers of polyhydric alcohols, such as 1,4-butanediol, or of polyalkylene glycols, such as polypropylene glycol; di- or poly-glycidyl ethers of cycloaliphatic polyols, such as 2,2-bis-(4-hydroxycyclohexyl)-propane; di- or poly-glycidyl ethers of polyhydric phenols, such as resorcinol, bis-(p-hydroxyphenyl)-methane, 2,2-bis-(p-hydroxyphenyl)-propane (diomethane), 2,2-bis-(4'-hydroxy-3',5'-dibromophenyl)-propane and 1,1,2,2-tetrakis-(p-hydroxyphenyl)-ethane, or condensation products of phenols and formaldehyde which have been obtained under acid conditions, such as phenol novolacs and cresol novolacs; and also di- or poly-(β-methylglycidyl) ethers of the above-mentioned polyalcohols and polyphenols; polyglycidyl esters and poly-(β-methylglycidyl) esters of polybasic carboxylic acids, such as phthalic acid, terephthalic acid, tetrahydrophthalic acid and hexahydrophthalic acid; N-glycidyl derivatives of amines, amides and heterocyclic nitrogen bases, such as N,N-diglycidylaniline, N,N-diglycidyltoluidine and N,N,N',N'-tetraglycidyl-bis-(p-aminophenyl)-methane; triglycidyl isocyanurate; N,N'-diglycidylethyleneurea; N,N'-diglycidyl-5,5-dimethylhydantoin, N,N'-diglycidyl-5-isopropyl-hydantoin and N,N'-diglycidyl-5,5-dimethyl-6-isopropyl-5,6-dihydrouracil.

If desired, active diluents, such as, for example, styrene oxide, butyl glycidyl ether, isooctyl glycidyl ether, phenyl glycidyl ether, cresyl glycidyl ether and glycidyl esters of synthetic, highly branched aliphatic monocarboxylic acids, which in the main are tertiary, can be added to the curable mixtures in order to lower the viscosity.

Curing accelerators can also be employed during curing; such accelerators are, for example, tertiary amines, the salts thereof or quaternary ammonium compounds, for example 2,4,6-tris-(dimethylaminomethyl)-phenol, benzyldimethylamine, 1-methylimidazole, 2-ethyl-4-methyl-imidazole, 4-aminopyridine and triamylammonium phenolate; or alkali metal alcoholates, such as, for example, sodium hexanetriolate. Curing of the mixtures, according to the invention, of a curing agent (b), according to the definition, the epoxide resin (a) and, optionally, a vinyl compound (c) is appropriately carried out in the temperature range from 20° C.-250° C., preferably from 100° C.-220° C.

Curing of mixtures which contain a polyepoxide compound (a), a curing agent (b) and a vinyl compound (c) is advantageously carried out in the presence of free radical initiators which are in themselves known, such as inorganic and organic peroxides or azo compounds, for example hydrogen peroxide, potassium peroxydisulphate, tert.-butyl hydroperoxide, di-tert.-butyl peroxide, peracetic acid, benzoyl peroxide, diacyl peroxides, cumene hydroperoxide, tert.-butyl perbenzoate, tert.-alkyl peroxycarbonates and $\alpha,\alpha'$-azo-isobutyronitrile. It is also possible to use redox systems, for example mixtures of peroxides, such as hydrogen peroxide, and a reducing agent, such as divalent iron ions, in place of the initiators mentioned. The free radical initiators and redox systems are generally employed in amounts of 0.01 to 5% by weight, preferably 0.01 to 1.5% by weight, based on the total weight of the curing agent mixture.

It is also possible, in a known manner, to carry out the curing in two or more stages, the first curing stage being carried out at a relatively low temperature and the post-curing being carried out at a relatively high temperature.

If desired, curing can also be carried out in 2 stages in such a way that the curing reaction is first discontinued prematurely or the first stage is carried out at a slightly elevated temperature, in which case a curable precondensate which is still fusible and/or soluble (a so-called "B stage") is obtained from the epoxide component (a), the curing agent (b) and, optionally, the vinyl compound (c). A precondensate of this type can be used, for example, to manufacture "prepregs", moulding compositions or, in particular, sintering powders.

As used here, the expression "curing" denotes the conversion of the soluble polyepoxides, which are either liquid or fusible, into solid, insoluble and infusible three-dimensionally crosslinked products and materials and, in particular, this conversion is as a rule effected with simultaneous shaping to give shaped articles, such as castings, compression mouldings and laminates, or to produce impregnated products, coatings, lacquer films or adhesive bonds.

The curable mixtures according to the invention can also contain suitable plasticisers, such as dibutyl phthalate, dioctyl phthalate or tricresyl phosphate.

Furthermore, extenders, fillers and reinforcing agents, such as, for example, coal tar, bitumen, textile fibres, glass fibres, asbestos fibres, boron fibres, carbon fibres, mineral silicates, mica, ground quartz, titanium dioxide, hydrated aluminium oxide, bentonites, kaolin, silica aerogel or metal powders, such as aluminium powder or iron powder, and also pigments and dyestuffs, such as carbon black, coloured oxide pigments, titanium dioxide and the like, can be added to the curable mixtures according to the invention, in any desired phase prior to curing. Furthermore, other customary additives, for example flameproofing agents, such as antimony trioxide, thixotropic agents or flow control agents, such as silicones, waxes or stearates (some of which are also used as mould release agents) can also be added to the curable mixtures.

The manufacture of the curable mixtures according to the invention can be carried out in the customary manner with the aid of known mixing equipment (stirrers, kneaders, roll mills and the like).

The curable epoxide resin mixtures according to the invention are employed, above all, in the fields of surface protection, electrical engineering and laminating processes and in the building trade. They can be used, in the unfilled or filled state, in a formulation which in each case is suited to the particular application, for example as paints or lacquers, as moulding compositions, dipping resins, casting resins, injection moulding formulations, impregnating resins and adhesives and as tool resins, laminating resins, sealing compositions and surface fillers, floor covering compositions and binders for mineral aggregates.

The following epoxide resin was used for the manufacture of curable mixtures, which is described in the application examples:

Epoxide resin A

An epoxide resin (industrial product) which is liquid at room temperature, has an epoxide content of 5.12-5.54 epoxide equivalents/kg and was manufactured by a condensation reaction of 2,2-bis-(p-hydroxyphenyl)-propane with a stoichiometric excess of epichlorohydrin in the presence of alkali, and which in the main consists of the monomeric diglycidyl ether of the formula

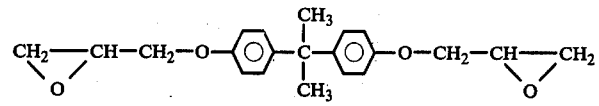

Vicosity (Hoeppler) at 25° C.: 9,000-13,000 cP.

In order to determine the mechanical properties of the curable mixtures described in the examples which follow, 4 mm thick sheets were manufactured. The test pieces for determination of the heat distortion point according to ISO/R 75 (DIN 53,461) and the flexural strength and the deflection according to VSM 77,103 were machined from the sheets.

Sheets 1 mm and 2 mm thick were manufactured in order to determine the electrical properties (dielectric loss factor according to DIN 53,483 and the dielectric constant according to DIN 53,483).

The imidyl derivatives, according to the invention, of the formula I are suitable for the manufacture of cross-linkable polymers and of polymers which may already be partly cross-linked, especially for the manufacture of polycondensation products, by reacting them in a manner which is in itself known with substantially stoichiometric amounts of diamines, diols or aminoalcohols, or derivatives thereof, and optionally in the presence of further di-, tri- or tetra-carboxylic acid derivatives, or functional derivatives thereof.

Crosslinkable polymers can also be obtained by homopolymerisation of compounds of the formula I or by copolymerisation of compounds of the formula I with vinyl comonomers, such as vinyl chloride, vinylidene chloride, vinyl acetate, styrene and derivatives thereof, methacrylic acid derivatives, acrylonitrile or divinylbenzene.

By suitable choice of the comonomers or of the polycondensation components it is possible to manufacture polymers which have any desired number, and a statistical distribution, of the crosslinkable or crosslinked groups and to convert these polymers into polymers which have a degree of cross-linking suited to the particular application. The polymers obtained are distinguished by good processability and, above all, by good solubility in the customary organic solvents and good fusibility and are suitable for the manufacture of shaped articles of very diverse types, for example fibres, films (thin or thick) and compression mouldings.

A. Preparation Examples

Example 1

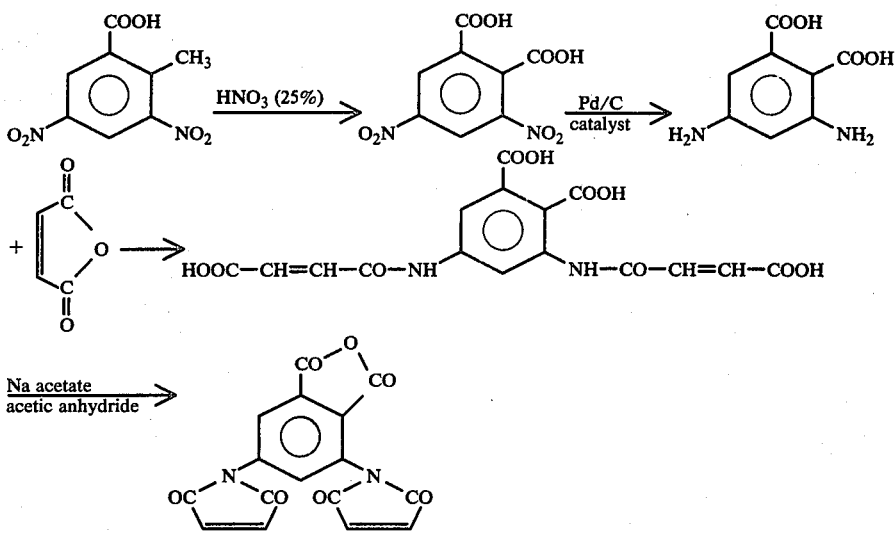

813 g (3.59 mols) of 3,5-dinitro-o-toluic acid and 8.250 ml of 25% strength nitric acid are heated to 150° C. for 5 hours in an autoclave. After cooling the reaction mixture to 25° C., excess 3,5-dinitro-o-toluic acid is filtered off. The filtrate is concentrated to dryness at 50° C. in a rotary evaporator, the residue is dried for 12 hours at 120° C./100 mm Hg and then boiled in 2,700 ml of benzene for 3 hours, whilst stirring, and, finally, the mixture is filtered hot. After drying the reaction product for 36 hours at 100° C./100 mm Hg, 495 g of 3,5-dinitrophthalic acid (53.8% of theory based on the 3,5-dinitro-o-toluic acid employed and 86.4% of theory when the excess 3,5-dinitro-o-toluic acid, which is recovered, is taken into account) are obtained.

76.8 g (0.33 mol) of 3,5-dinitrophthalic acid are hydrogenated at 30° C., in 2,400 ml of dioxane, in the presence of 8 g of a palladium-on-charcoal catalyst containing 5% by weight of palladium. The reaction solution is filtered and 91.2 g (0.93 mol) of maleic anhydride are then added to the filtrate and the mixture is stirred for 12 hours at 20°–25° C. and finally is concentrated to dryness at 50° C. in a rotary evaporator. The residue is first extracted with twice 400 ml of hot ethyl acetate and then dried for 12 hours at 70° C./100 mm Hg. 74.5 g (63.5% of theory) of 3,5-bis-maleamidyl-phthalic acid are obtained.

23.5 g (0.06 mol) of this 3,5-bis-maleamidyl-phthalic acid are mixed with 1.14 g of anhydrous sodium acetate and 96 ml of acetic anhydride and the mixture is heated to 80° C. for 35 minutes. The resulting solution is evaporated to dryness and the residue is after-dried at 60° C./0.1 mm Hg. The residue is extracted with three times 200 ml of ethyl acetate. The extracts are combined and filtered through 2 g of animal charcoal, the filtrate is evaporated to half its volume and 500 ml of cyclohexane are then added. The reaction product which has crystallised out is filtered off and dried for 12 hours at 80° C./0.1 mm Hg. 12 g (59.14% of theory) of crystalline 3,5-bis-(maleimidyl)-phthalic anhydride are obtained; melting point 246°–247° C. (with decomposition).

Analysis for $C_{16}H_6N_2O_7$ (molecular weight 338.24): calculated: C, 56.82%; H, 1.79%; N, 8.28%. Found: C, 56.70%; H, 2.00%; N, 8.10%.

Example 2

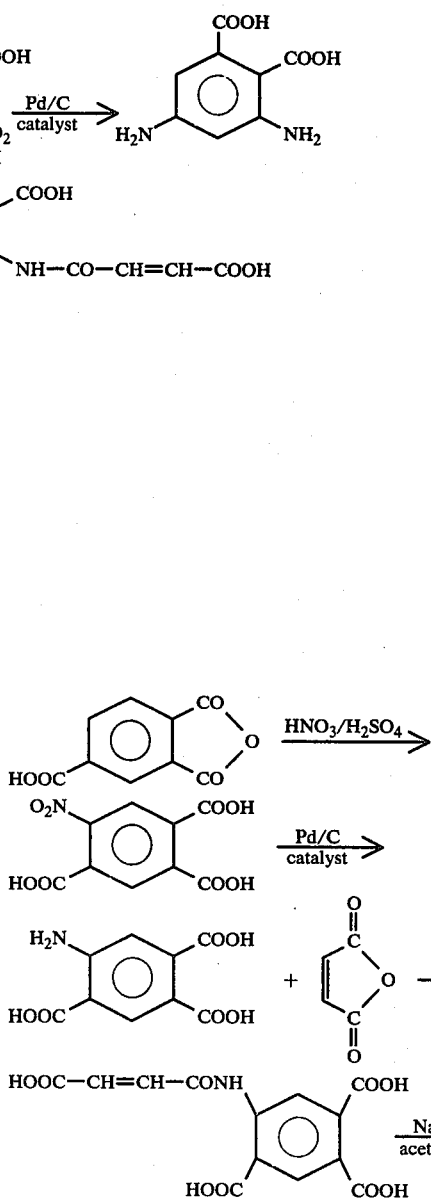

-continued

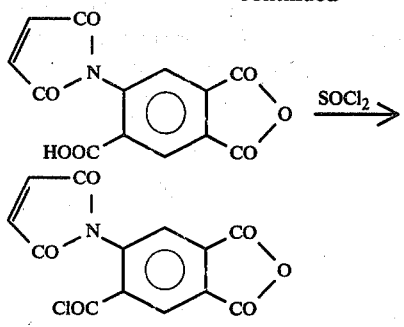

96 g (0.5 mol) of trimellitic anhydride in 1,360 ml of H₂SO₄ (97% strength) and 680 ml of 100% strength HNO₃ are heated at 97° C. for 19 hours. The reaction solution is then poured onto 2,000 g of ice and the mixture is stirred for 2 hours at −5° C. The 5-nitro-trimellitic acid which has crystallised out is dissolved in 125 ml of hot water and the solution is rendered basic (pH 9) with 30% strength aqueous sodium hydroxide solution and finally acidified to pH 1 with concentrated hydrochloric acid. The reaction solution is then evaporated to dryness and the residue is extracted with twice 400 ml of dioxane. The extracts are combined and evaporated to dryness, the residue is boiled with 120 ml of benzene, the mixture is filtered and the product is dried. 66 g (51.7% of theory) of 5-nitro-trimellitic acid are obtained.

102 g (0.4 mol) of this 5-nitro-trimellitic acid are hydrogenated at 30° C. in 1,000 ml of dioxane in the presence of 10 g of a palladium-on-charcoal catalyst containing 5% by weight of palladium. The reaction solution is filtered and 46.8 g (0.48 mol) of maleic anhydride are then added to the filtrate. The reaction mixture is left to stand at room temperature (20°-25° C.) for 12 hours and then evaporated to dryness at 60° C. in a rotary evaporator. The residue is twice heated to the boil with, in each case, 400 ml of ethyl acetate, whilst stirring, and is then filtered off and dried at 80° C./100 mm Hg for 24 hours. 105 g (81.3% of theory) of 5-maleamidyl-trimellitic acid are obtained.

32.3 g (0.1 mol) of the 5-maleamidyl-trimellitic acid are mixed with 1.6 g of anhydrous sodium acetate and 83 ml of acetic anhydride and the mixture is heated to 80° C. for 30 minutes. The resulting solution is evaporated to dryness and the residue is after-dried at 50° C./0.05 mm Hg. 200 ml of thionyl chloride are added to the residue and the mixture is heated to 80° C. for 2.5 hours. The reaction mixture is then concentrated to dryness, 150 ml of benzene are added to the residue, the mixture is filtered and the filtrate is evaporated and, finally, the residue is dried at 80° C./0.1 mm Hg. 50 ml of benzene are added to the residue and the mixture is stirred intensively for 4 hours at 20°-25° C. A crystal slurry forms and is filtered and the crystals are then washed with 20 ml of a 1:3 mixture by volume of cyclohexane and benzene and finally dried for 12 hours at 80° C./0.1 mm Hg. 18.31 g (60% of theory) of crystalline 5-maleimidyl-trimellitic anhydride-chloride are obtained; melting point 143°-144° C.

Analysis for $C_{13}H_{14}NO_6Cl$ (molecular weight 305.61): calculated: C, 51.09%; H, 1.32%; N, 4.58%. Found: C, 51.09%; H, 1.44%; N, 4.57%.

EXAMPLE 3

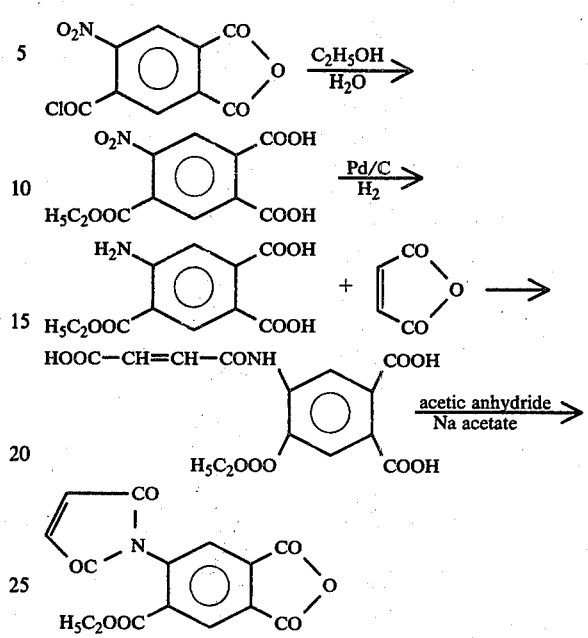

102 g (0.4 mol) of 5-nitro-trimellitic acid are dissolved in 150 ml of acetic anhydride at 130°-140° C. The resulting solution is evaporated to dryness. 280 ml of benzene are added to the residue, the mixture is stirred for 12 hours and filtered and the product is dried at 60° C. in a drying cabinet. 85.7 g (78.5% of theory) of 5-nitro-trimellitic anhydride are obtained; melting point 232° C.

85.36 g (0.36 mol) of 5-nitro-trimellitic anhydride are suspended in 200 ml of benzene and 52.4 ml (0.72 mol) of thionyl chloride and 1 ml of N,N-dimethylformamide are added. The reaction mixture is heated until a clear solution has formed (about 60 minutes). The reaction mixture is then cooled to about 15° C., whereupon 5-nitro-trimellitic anhydride-chloride crystallises out. This is filtered off, washed with 60 ml of cyclohexane and dried over phosphorus pentoxide at 50° C. in a drying cabinet. 77 g (83.5% of theory) of 5-nitro-trimellitic anhydride-chloride are obtained; melting point 90°-91° C.

61.33 g (0.24 mol) of 5-nitro-trimellitic anhydride-chloride are dissolved in 120 ml of dioxane and 13.94 ml (0.24 mol) of ethanol are added, whilst stirring. The reaction mixture is stirred at 25° C. for 12 hours, then heated to 80° C. for 1 hour and finally evaporated to dryness.

The residue is dissolved in 180 ml of dioxane and 100 ml of water are added dropwise and after one hour the mixture is evaporated to dryness. The resulting residue is finely suspended in 100 ml of benzene, the suspension is filtered and the product is dried at 80° C. in a drying cabinet. 60.5 g (89% of theory) of 5-nitro-trimellitic acid ethyl ester are obtained; melting point 189°-191° C.

65.13 g (0.23 mol) of 5-nitro-trimellitic acid ethyl ester are dissolved in 150 ml of dioxane and hydrogenated at 30° C. in the presence of 6.5 g of a palladium-on-charcoal catalyst containing 5% by weight of Pd. The reaction solution is filtered, 27 g of maleic anhydride are then added to the filtrate and the mixture is left to stand for 12 hours at 20°-25° C. The solution is then evaporated at 40°-60° C. and 250 ml of diethyl ether are added to the oily residue, whilst stirring. 5-Maleamidyl-trimellitic acid ethyl ester, which separates out as a fine white precipitate, is filtered off and dried at 50° C. in a drying cabinet. 76.7 g (95% of theory) of the said ester are obtained; melting point 142°-144° C.

58 g (0.165 mol) of 5-maleamidyl-trimellitic acid ethyl ester are introduced slowly, in the course of 15 minutes, at 80° C. into a mixture of 65 ml of acetic anhydride and 14.5 g of sodium acetate. The reaction mixture is stirred at this temperature for 3 hours and then concentrated to dryness and the residue is extracted with three times 200 ml of toluene. The combined toluene extracts are evaporated to dryness, finally at 50° C./0.2 mm Hg. The solid residue is dissolved in 100 ml of hot toluene and the solution is filtered. The 5-maleimidyl-trimellitic anhydride-ethyl ester, which has crystallised out after the solution has cooled, is filtered off and dried at 70° C. in a drying cabinet. 39.6 g (60% of theory) of 5-maleimidyl-trimellitic anhydride-ethyl ester with a melting point of 178°-179° C. are obtained. Analysis for $C_{15}H_9NO_7$ (molecular weight 315.24): calculated: C, 57.14%; H, 2.88%; N, 4.44%. Found: C, 56.76%; H, 3.03%; N, 4.35%.

EXAMPLE 4

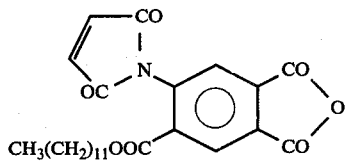

51.11 g (0.2 mol) of 5-nitro-trimellitic anhydride-chloride are dissolved in 100 ml of dioxane. A solution of 37.27 g (0.2 mol) of n-dodecanol in 80 ml of dioxane is then added dropwise and the reaction mixture is heated to 80° C. for 2½ hours. The reaction mixture is then evaporated to dryness, the residue is again dissolved in 150 ml of dioxane and 10 ml of water are added dropwise, whilst stirring. After 1 hour the reaction solution is again evaporated to dryness and 80 ml of benzene are added to the residue. After stirring for 12 hours, the resulting fine suspension is filtered and the product is dried at 70° C. in a drying cabinet. 76 g (90% of theory) of 5-nitro-trimellitic acid dodecyl ester are obtained; melting point 148° C.

78.06 g (0.1843 mol) of 5-nitro-trimellitic acid dodecyl ester are dissolved in 250 ml of dioxane and hydrogenated at 25° C. in the presence of 8 g of a palladium-on-charcoal catalyst containing 5% by weight of Pd. The catalyst is removed by filtration. 22 g of maleic anhydride are added to the clear reaction solution and the mixture is stirred for 12 hours at 20-25° C. After distilling off the dioxane at 40-60° C., an oily residue is obtained and 200 ml of diethyl ether are added to this. The resulting white suspension is filtered and the product is dried at 50° C. in a drying cabinet. 63 g (69.5% of theory) of 5-maleamidyl-trimellitic acid dodecyl ester are obtained; melting point 133° C.

61.44 g (0.125 mol) of 5-maleamidyl-trimellitic acid dodecyl ester are introduced in portions, in the course of 15 minutes, whilst stirring, into a suspension, which has been heated to 80° C., of 8.3 g of anhydrous sodium acetate in 50 ml of acetic anhydride.

The reaction mixture is subsequently stirred for a further 30 minutes at the same temperature and then evaporated to dryness. The residue is extracted with twice 250 ml of dioxane. The combined extracts are evaporated and 200 ml of diethyl ether are added to the oily residue, whilst stirring. A fine crystalline suspension is formed, this is filtered and the product is dried at 50° C. in a drying cabinet. 23.5 g (41% of theory) of 5-maleimidyl-trimellitic anhydride-dodecyl ester are obtained; melting point 86° C.

Analysis for $C_{25}H_{29}NO_7$ (molecular weight 455.51): calculated: C,65.92%; H,6.42%; N,3.07%. Found: C,65.64%; H,6.56%; N,3.07%.

Example 5

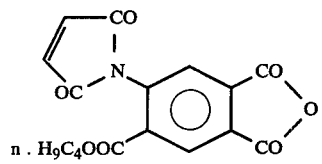

In accordance with the procedure described in Example 3, 5-nitro-trimellitic anhydride-chloride is reacted with the stoichiometric amount of n-butyl alcohol. After further reaction as described in Example 3, 5-maleimidyl-trimellitic anhydride-n-butyl ester is obtained in the form of a very viscous oil.

Analysis for $C_{17}H_{13}NO_7$ (molecular weight 343.29): calculated: C,59.48%; H,3.82%; N,4.08%. Found: C,59.37%; H,3.71%; N,3.84%.

IR spectrum in dioxane: 1850 cm$^{-1}$, 1790 cm$^{-1}$ (—CO—O—CO—) and 1730 cm$^{-1}$, (—CO—N—CO—).

NMR spectrum $\delta$ = 7.35 ppm

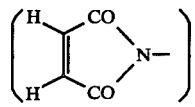

Example 6

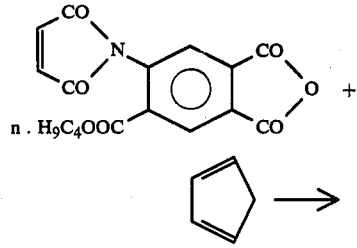

7.33 g (0.213 mol) of the 5-maleimidyl-trimellitic anhydride-n-butyl ester prepared according to Example 5 are dissolved in 25 ml of toluene. 1.552 g (0.0235 mol) of freshly distilled cyclopentadiene are then added. After leaving the reaction mixture to stand for 12 hours at 25° C., the solvent is evaporated and the oily residue is dried for 5 hours at 80° C./0.2 mm Hg.

8.72 g (quantitative yield) of 5-endomethylenetetrahydrophthalimidyl-trimellitic 1,2-anhydride-4-n-butyl ester are obtained in the form of a very viscous oil.

Analysis for $C_{22}H_{19}NO_7$ (molecular weight 409.37): calculated: C,64.54% H;4.67%; N,3.42%. Found: C,64.04%; H,4.86%, N,3.26%.

B. Application Examples

Example I 1.44 g of epoxide resin A (epoxide content 5.20 epoxide equivalents/kg) and 2.25 g of the 3,5-bis-(maleimidyl)-phthalic anhydride prepared according to Example 1 (corresponding to 0.9 mol of the anhydride per 1 equivalent of epoxide groups) are mixed and the mixture is warmed to 120° C. The mixture is initially stirred vigorously and then kept at 120° C. for 40 minutes. After cooling, the mixture is finely powdered, introduced into a compression mould for circular discs, which has been prewarmed to 185° C., and moulded by the compression process at 185° C. for 30 minutes under 225 kg/cm². Well consolidated, transparent mouldings are obtained and are post-cured in an oven for 3 hours at 150° C. and for 5 hours at 220° C.; dielectric loss factor Tg δ of the mouldings according to DIN 53,483 at 180° C. (50 Hz) = 0.018; dielectric constant ε according to DIN 53,483 at 180° C. = 3.8.

Example II 7.68 g of epoxide resin A (epoxide content 5.20 epoxide equivalents/kg) and 11.35 g of the 5-maleimidyl-trimellitic 1,2-anhydride-4-ethyl ester prepared according to Example 3 (corresponding to 0.9 mol of the anhydride per 1 equivalent of epoxide groups) are mixed and the mixture is warmed to 165° C. for 10 minutes, whilst stirring. A clear solution is formed and, in order to produce 4 mm thick sheets, is cast into an aluminium mould, which has been prewarmed to 150° C. Curing is effected in a circulating air oven, first for 3 hours at 150° C. and then for 5 hours at 220° C. Transparent, bubble-free castings are obtained; heat distortion point of the castings according to ISO/R 75 (DIN 53,461) = 194° C.; flexural strength according to VSM 77,103 = 48 N/mm²; deflection according to VSM 77,103 = 2 mm.

Example III 4.80 g of epoxide resin A (epoxide content 5.20 epoxide equivalents/kg) and 10.25 g of the 5-maleimidyl-trimellitic 1,2-anhydride-4-lauryl ester prepared according to Example 4 (corresponding to 0.9 mol of the anhydride per 1 equivalent of epoxide groups) are mixed and the mixture is warmed to 100° C. for 20 minutes, whilst stirring. A clear solution is formed and is processed according to the procedure described in Example II to give transparent, bubble-free castings; heat distortion point of the castings according to ISO/R 75 (DIN 53,461) = 132° C.; flexural strength according to VSM 77,103 = 57 N/mm²; deflection according to VSM 77,103 = 4 mm [ISO/R = International Standards Organisation/Recommendations; VSM = Verein Schweizerischer Maschinenindustrieller (Association of Swiss Machine Industrialists)].

Example IV 1.92 g of epoxide resin A (epoxide content 5.20 epoxide equivalents/kg) and 2.83 g of the 5-maleimidyl-trimellitic 1,2-anhydride-4-ethyl ester prepared according to Example 3 (corresponding to 0.9 mol of the anhydride per 1 equivalent of epoxide groups) are mixed and the mixture is warmed to 110° C. The mixture is initially stirred vigorously and then kept at 110° C. for 15 minutes. After cooling, the mixture is finely powdered and sieved. The powder is introduced into a compression mould for circular discs, which has been prewarmed to 220° C., and moulded by the compression process at 220° C. for 25 minutes under 330 kg/cm². Well consolidated, transparent mouldings are obtained and are post-cured for 5 hours at 220° C. in an oven. The dielectric loss factor Tg δ, according to DIN 53,483, of these mouldings is 0.009 at 180° C. (50 Hz) and the dielectric constant ε according to DIN 53,483 at 180° C. (50 Hz) = 3.6 (DIN = Deutsche Industrie Norm (German Industrial Standard)).

Example V 7.931 g (0.040 mol) of 4,4'-diaminodiphenylmethane are dissolved in 160 ml of anhydrous N,N-dimethylacetamide (DMA) under a nitrogen atmosphere in a sulphonation flask. This solution is cooled to −15° C. to −20° C. A mixture of 6.738 g (0.032 mol) of trimellitic anhydride-chloride and 2.445 g (0.008 mol) of the 5-maleimidyl-trimellitic anhydride-chloride prepared according to Example 2, in the solid form, is then added in portions, whilst stirring, at such a rate that the temperature does not exceed −15° C. When the addition is complete, the solution is stirred for a further 1 hour at 20–25° C.

Part of the resulting polymer solution is cast onto an aluminium foil and heated as follows: 30 minutes each at 70° C./20 mm Hg, 90° C./20 mm Hg, 110° C./20 mm Hg, 130° C./20 mm Hg and 150° C./20 mm Hg, 1 hour at 180° C./10⁻¹ mm Hg and 1 hour at 200° C./10⁻¹ mm Hg. A clear, mechanically strong coating of the crosslinked polyamide-imide is obtained. A transparent, flexible film of good mechanical strength is obtained by dissolving off the aluminium foil with dilute hydrochloric acid.

Example VI 3.056 g (0.01 mol) of 5-maleimidyl-trimellitic anhydride-chloride are added, in portions, whilst stirring and under a nitrogen atmosphere at −15° C., to a solution of 2.182 g (0.02 mol) of 3-aminophenol in 30 ml of anhydrous DMA and the mixture is stirred for a further 30 minutes. 2.03 g (0.01 mol) of isophthalic acid dichloride in the solid form are then added at the same temperature, the reaction mixture is stirred for 30 minutes and 3.033 g (0.03 mol) of triethylamine are then added dropwise. The cooling bath is removed and the reaction mixture is stirred for 2 hours at 20–25° C. The triethylamine hydrochloride which has precipitated out is then filtered off. The resulting polymer solution is cast onto an aluminium foil and heated as described in Example V. A transparent coating of the crosslinked polyesteramide-imide is obtained.

Example VII 7.80 g of epoxide resin A (epoxide content 5.13 epoxide equivalents/kg) and 12.36 g of the 5-maleimidyl-trimellitic 1,2-anhydride-4-n-butyl ester prepared according to Example 5 (corresponding to 0.9 mol of the anhydride per 1 equivalent of epoxide groups) are mixed and the mixture is warmed to 100° C. for 15 minutes, whilst stirring. 1.15 g (0.012 mol) of styrene and 1 drop of di-tert.-butyl peroxide are added to the resulting clear solution and the mixture is poured into an aluminium mould for sheets, which has been prewarmed to 120° C. Curing is effected in a circulating air oven, first for 3 hours at 120° C. and then for 13 hours at 160° C. Transparent, bubble-free castings are obtained. Dielectric loss factor Tg δ, according to DIN 53,483, of the castings at 180° C. = 0.0144; dielectric constant ε according to DIN 53,483 at 180° C. = 4.4.

Example VIII 3.90 g of epoxide resin A (epoxide content 5.13 epoxide equivalents/kg) and 7.37 g of the 6-endomethylenetetrahydrophthalimidyl-trimellitic anhydride-4-n-butyl ester prepared according to Example 5 (corresponding to 0.9 mol of the anhydride per 1 equivalent of epoxide groups) are mixed and the mixture is warmed to 120° C. for 10 minutes, whilst stirring. In order to produce 2 mm thick sheets, the resulting clear solution is poured into an aluminium mould, which has been warmed to 150° C., and cured as described in Application Example II. A transparent, bubble-free casting is obtained. Dielectric loss factor Tg δ, according to DIN 53,483, of the castings at 180° C. = 0.0188; dielectric constant ε according to DIN 53,483 at 180° C. = 4.0.

We claim:

1. An imidyl-benzenetricarboxylic acid compound of the formula I

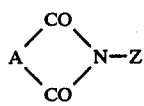

wherein
A denotes a radical of the formula

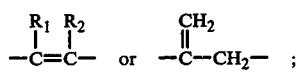

$R_1$ and $R_2$ independently of one another denote hydrogen, chlorine or bromine; Z denotes a radical of the formula

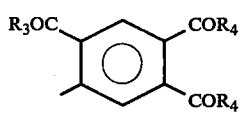

$R_4$ denotes hydroxyl, phenoxy, phenoxy substituted by one or two nitro groups, by one alkyl of 1 to 2 carbon atoms, by one alkoxy of 1 to 2 carbon atoms or by two to five halogen atoms, alkoxy with 1 to 18 carbon atoms or an $-O^-M^+$ group, in which $M^+$ represents an alkali metal cation, a trialkylammonium cation with 3 to 24 carbon atoms or a lower alkyl quaternary ammonium cation; or the two $R_4$ groups conjointly denote the $-O-$ grouping; and when $R_4$ represents phenoxy, substituted phenoxy or alkoxy, or two $R_4$ groups conjointly denote $-O-$, $R_3$ denotes chlorine, hydroxyl, phenoxy, phenoxy substituted by one or two nitro groups, by one alkyl of 1 to 2 carbon atoms, by one alkoxy of 1 to 2 carbon atoms or by two to five halogen atoms, alkoxy with 1 to 18 carbon atoms or an $O^-M^+$ group; and when $R_4$ represents hydroxyl, $R_3$ denotes hydroxyl, phenoxy, phenoxy substituted by one or two nitro groups, by one alkyl of 1 to 2 carbon atoms, by one alkoxy of 1 to 2 carbon atoms or by two to five halogen atoms, or an alkoxy with 1 to 18 carbon atoms and, when $R_4$ represents an $-O^-M^+$ group, $R_3$ denotes an $-O^-M^+$ group, phenoxy, phenoxy substituted by one or two nitro groups, by one alkyl of 1 to 2 carbon atoms, by one alkoxy of 1 to 2 carbon atoms or by two to five halogen atoms; or alkoxy with 1 to 18 carbon atoms; and $M^+$ denotes an alkali metal cation, a trialkylammonium cation with 3 to 24 carbon atoms or a lower alkyl quaternary ammonium cation.

2. The compound as claimed in claim 1, having the formula

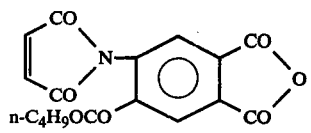

3. A compound of the formula I according to claim 1 wherein A represents the radical $-CH=CH-$.

4. A compound of the formula I according to claim 1, wherein Z denotes a radical of the formula

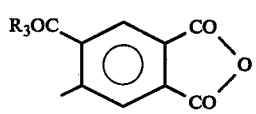

in which $R_3$ denotes a chlorine atom or an alkoxy group with 1-12 carbon atoms.

5. The compound as claimed in claim 1, having the formula

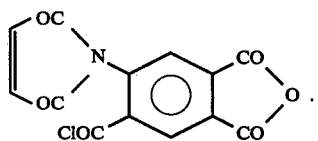

6. The compound as claimed in claim 1, having the formula

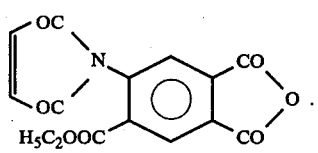

7. The compound as claimed in claim 1, having the formula

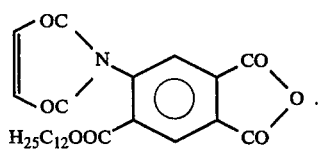

* * * * *